US010835206B2

(12) United States Patent
Bell et al.

(10) Patent No.: US 10,835,206 B2
(45) Date of Patent: Nov. 17, 2020

(54) WIRELESS ULTRASOUND PROBE PAIRING WITH A MOBILE ULTRASOUND SYSTEM

(71) Applicant: KONINKLIJKE PHILIPS N.V., Eindhoven (NL)

(72) Inventors: Kristy Bell, Eindhoven (NL); McKee Poland, Eindhoven (NL); Alexander Hunt, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 317 days.

(21) Appl. No.: 15/744,876

(22) PCT Filed: Jul. 4, 2016

(86) PCT No.: PCT/IB2016/053998
§ 371 (c)(1),
(2) Date: Jan. 15, 2018

(87) PCT Pub. No.: WO2017/009735
PCT Pub. Date: Jan. 19, 2017

(65) Prior Publication Data
US 2018/0263600 A1 Sep. 20, 2018

Related U.S. Application Data

(60) Provisional application No. 62/193,210, filed on Jul. 16, 2015.

(51) Int. Cl.
A61B 8/00 (2006.01)
G01S 7/00 (2006.01)
G01S 7/52 (2006.01)

(52) U.S. Cl.
CPC .......... *A61B 8/4472* (2013.01); *A61B 8/4411* (2013.01); *A61B 8/4427* (2013.01); *G01S 7/003* (2013.01); *G01S 7/52* (2013.01)

(58) Field of Classification Search
CPC .... A61B 8/4472; A61B 8/4411; A61B 8/4427
See application file for complete search history.

(56) References Cited

U.S. PATENT DOCUMENTS

| 5,229,993 A | 7/1993 | Larson, III |
| 5,997,479 A | 12/1999 | Savord et al. |
| 6,142,946 A | 11/2000 | Hwang et al. |

(Continued)

FOREIGN PATENT DOCUMENTS

WO 2004051882 A1 6/2004

*Primary Examiner* — Joseph M Santos Rodriguez

(57) ABSTRACT

A mobile ultrasound system will pair with a wireless ultrasound probe for exclusive communication between the two for an ultrasound exam when the wireless probe is brought to within a predetermined distance of the mobile ultrasound system. The ultrasound system determines that the wireless probe is within the predetermined distance from the strength of the signal received by the system from the wireless probe. Pairing can proceed automatically when a wireless probe is within the predetermined distance, or after a user actuates a control to initiate the pairing. The ultrasound system may display the identity of a probe within range on the display of the system for selection by the user so that the user will be confident that pairing will be done with the desired wireless probe.

15 Claims, 4 Drawing Sheets

(56) References Cited

U.S. PATENT DOCUMENTS

| | | | |
|---|---|---|---|
| 6,375,617 | B1 | 4/2002 | Fraser |
| 8,656,783 | B2 | 2/2014 | Randall et al. |
| 2008/0114241 | A1 | 5/2008 | Randall et al. |
| 2008/0242220 | A1 | 10/2008 | Wilson et al. |
| 2010/0168576 | A1 | 7/2010 | Poland et al. |
| 2013/0245451 | A1 | 9/2013 | Mochizuki et al. |
| 2014/0180110 | A1 | 6/2014 | Schmedling |
| 2016/0278739 | A1* | 9/2016 | Pelissier ............... A61B 8/465 |

* cited by examiner

WIRELESS ULTRASOUND PROBE PAIRING WITH A MOBILE ULTRASOUND SYSTEM

This application is the U.S. National Phase application under 35 U.S.C. § 371 of International Application No. PCT/IB2016/053998, filed on Jul. 4, 2016, which claims the benefit of Provisional Application Ser. No. 62/193,210, filed Jul. 16, 2015. These applications are hereby incorporated by reference herein.

This invention relates to medical diagnostic ultrasound systems and, in particular, to the pairing of a wireless ultrasound probe with the desired ultrasound system.

An ultrasound probe transmits ultrasound waves and receives ultrasonic echo signals with piezoelectric transducer elements that mechanically deflect when driven by a high voltage signal and convert vibrations due to received echo signals into electrical signals. Historically, ultrasound probes have been detachably connected to an ultrasound system by multiconductor cables which couple power and signals between the ultrasound system mainframe, which processes the echo signals into images, and the probe. To afford great latitude in positioning the ultrasound system, patient, and sonographer, these probe cables can be lengthy, extending upwards of three meters in length. But numerous sonographers do not like the inconvenience of the probe cable, which can be heavy, become tangled, and drag on the floor and get run over by the wheels when the ultrasound cart is moved or repositioned. The solution to this dilemma is a wireless ultrasound probe whereby communication with the system mainframe is done by r.f. communication and the probe is battery-powered. While wireless probes were first invented in 1998 as shown in U.S. Pat. No. 6,142,946 (Hwang et al.), their development and integration into mainstream diagnostic ultrasound has been slow. But aided by improved r.f. spectra availability, transceivers with greater bandwidth and performance, and smaller and lighter batteries, the prospects for wireless probes are brighter than ever before.

Before a wireless probe can be used to scan a patient, it must first be put into reliable two-way communication with the ultrasound system mainframe. A patent which has considered this step is U.S. Pat. No. 8,656,783 (Randall et al.), where this process is termed "linkup" as described in conjunction with FIG. 9 of the patent. This patent proposes to establish a communication link between a probe and an ultrasound system based upon the proximity of the two with each other and/or with other devices. For instance, if the probe and system are in proximity such that they are within r.f. range of each other, the communication link would be established. If there are multiple probes and/or systems within range, linkup would occur between the probe and system within closest proximity. The patent also proposes that the user may participate in the linkup by pressing a button to communicate a particular data sequence or character between the system and the probe to establish the linkup. The user may also select a desired probe type from a list of different types of probes, causing the system to send a linkup request to probes of the selected type. The patent goes on to say that the system and the probe may identify each other by their proximity (e.g., the linked probe is the one nearest the system), strength of signal communicated by the system (e.g., the probe links to the system sending the strongest signal), communication of a predetermined identifier, or the absence of any other probes. Once a communication link is established, it will endure for at least one operating session or over some predetermined period of time.

The list of linkup factors and possibilities proposed by Randall et al., however, does not fully consider the unlimited portability of wireless probes in a hospital or clinic, and the interactions between sonographers in a setting with many systems and probes, as is common in many clinical practices today. Simply linking the probe in closest proximity to a system becomes ambiguous when sonographer A, with a probe in the pocket of her lab coat, comes over to speak with sonographer B at sonographer B's ultrasound system. When sonographer B puts down her probe to have a dialog with sonographer A, the system will link with the now nearer probe in sonographer A's pocket, disrupting sonographer B's exam and leading to confusion. Linking with a probe that come into range, or even with the probe in closest proximity, is undesirable. If the sonographer takes a lunch break before a defined operating session has concluded, should the probe and system try to maintain the linkup? If a sonographer walks by with another mobile ultrasound system during the break, the linkup of one or both systems to the probe can change. If the predetermined time period expires before the sonographer has finished the exam, should the probe and system end their communication? These dilemmas, unaddressed by the Randall et al. patent, will be posed repeatedly in the large diagnostic labs in common practice today, and must be addressed and resolved so that the proper probe is quickly paired with the proper ultrasound system and remains in communication with it without interruption at all times during the diagnostic exam.

In some aspects, the present invention provides methods for pairing a wireless ultrasound probe with a mobile ultrasound system. The methods can include locating a wireless ultrasound probe with a radio within a predetermined distance of a mobile ultrasound system with a radio, determining, at the mobile ultrasound system, that the wireless ultrasound probe present is within the predetermined distance, and pairing the wireless ultrasound probe and mobile ultrasound system to be in communication with each other.

In certain aspects, the predetermined range is one meter, or the predetermined range is a distance of one meter from an antenna of the mobile ultrasound system radio. In some aspects, the ultrasound system radio and the wireless probe radio are both ultra wideband transceivers, such as WiFi (802.11) standard transceivers.

In some aspects, the determining step of the methods can further include receiving with the ultrasound system radio a radio signal from the wireless probe and producing a signal indicating the strength of the received signal. The determining step can further include comparing the signal indicating the strength of the received signal to a threshold voltage. The producing step can further include producing an RSSI signal by the ultrasound system radio. In certain aspects, the threshold voltage is equal to a signal indicating the strength of the received signal when the wireless probe is at the predetermined distance from the ultrasound system.

In certain aspects, the methods can further include maintaining a communication link established by the pairing until the user affirmatively ends it; or the wireless ultrasound probe is turned off; or the wireless ultrasound probe has been out of range of the mobile ultrasound system for a long period of time; or the communication of new data over the link has been idle for a preset period of time.

In some aspects, the methods can further include conducting an ultrasound exam with the paired wireless ultrasound probe and mobile ultrasound system; suspending the ultrasound exam; and actuating a user control of the mobile ultrasound system to maintain the paired communication during suspension of the ultrasound exam.

In certain aspects, the present invention can include a method for pairing one of a plurality of wireless ultrasound probes that are within radio range of a mobile ultrasound system with the mobile ultrasound system that includes locating a plurality of wireless ultrasound probes, each having a radio, within radio range of a mobile ultrasound system having a radio; receiving, with the radio of the mobile ultrasound system, a unique identifier signal from each of the wireless ultrasound probes; displaying on a display of the mobile ultrasound system the identities of the wireless ultrasound probes in correspondence with the unique identifier signals; and pairing a particular wireless ultrasound probe and the mobile ultrasound system by selecting the displayed identity of the particular wireless ultrasound probe.

In some aspects, the displaying step can include displaying the identities of the wireless ultrasound probes in order of the strength of signals received from the probes, and/or the displaying can include displaying the identity of a wireless ultrasound probe only if it is within a predetermined distance of the mobile ultrasound system; and wherein pairing further comprises selecting the displayed wireless ultrasound probe for pairing.

In certain aspects, the methods can include maintaining a communication link established by the pairing until the user affirmatively ends it; or the particular wireless ultrasound probe is turned off; or the particular wireless ultrasound probe has been out of range of the mobile ultrasound system for a long period of time; or the communication of new data over the link has been idle for a preset period of time.

In accordance with the principles of the present invention, a wireless probe is paired to be in r.f. communication with a mobile ultrasound system when the probe is brought within a predetermined distance of the ultrasound system, as indicated by the received signal strength indication (RSSI) at the ultrasound system's radio. The radio type used by the probe and the ultrasound system can be ultra wideband (UWB) transceivers, WiFi (IEEE 802.11) transceivers, or transceivers of some other standard. The probe transmits an identifier which uniquely identifies that probe. The signal transmitted by the probe is calibrated to the predetermined distance so that, when the probe is at or closer than the predetermined distance with the ultrasound system, the RSSI received and measured at the system will be at or above a predetermined threshold. When this condition occurs, the system automatically selects the probe's unique transmitted identifier as the one with which to establish communication for an ultrasound procedure. The pairing process can be set to occur automatically when a wireless probe is brought within the predetermined range and the system is not currently in communication with another probe, or can be initiated by the user pressing a button on the system when a probe is within the predetermined range. The communication link is maintained until the user affirmatively ends it, or until the wireless probe is turned off, or until the wireless probe has been out of range of the ultrasound system for a long period of time, or for as long as data is being communicated over the link, or until after the communication of new data over the link has been idle for a preset period of time, i.e., the idle link times out. In accordance with a further aspect of the present invention, the user can select a wireless probe with which to pair from a list of probes on the display of the ultrasound system. The displayed list is a list of the probes currently found to be within r.f. communication range of the ultrasound system, and is preferably displayed on the screen in signal strength order, that is, the probe nearest to the system is at the top of the list. The user then selects a probe to pair to the system and, if the probe is not presently linked to be in communication with another system, the communication link to that probe is established.

Figure 1:
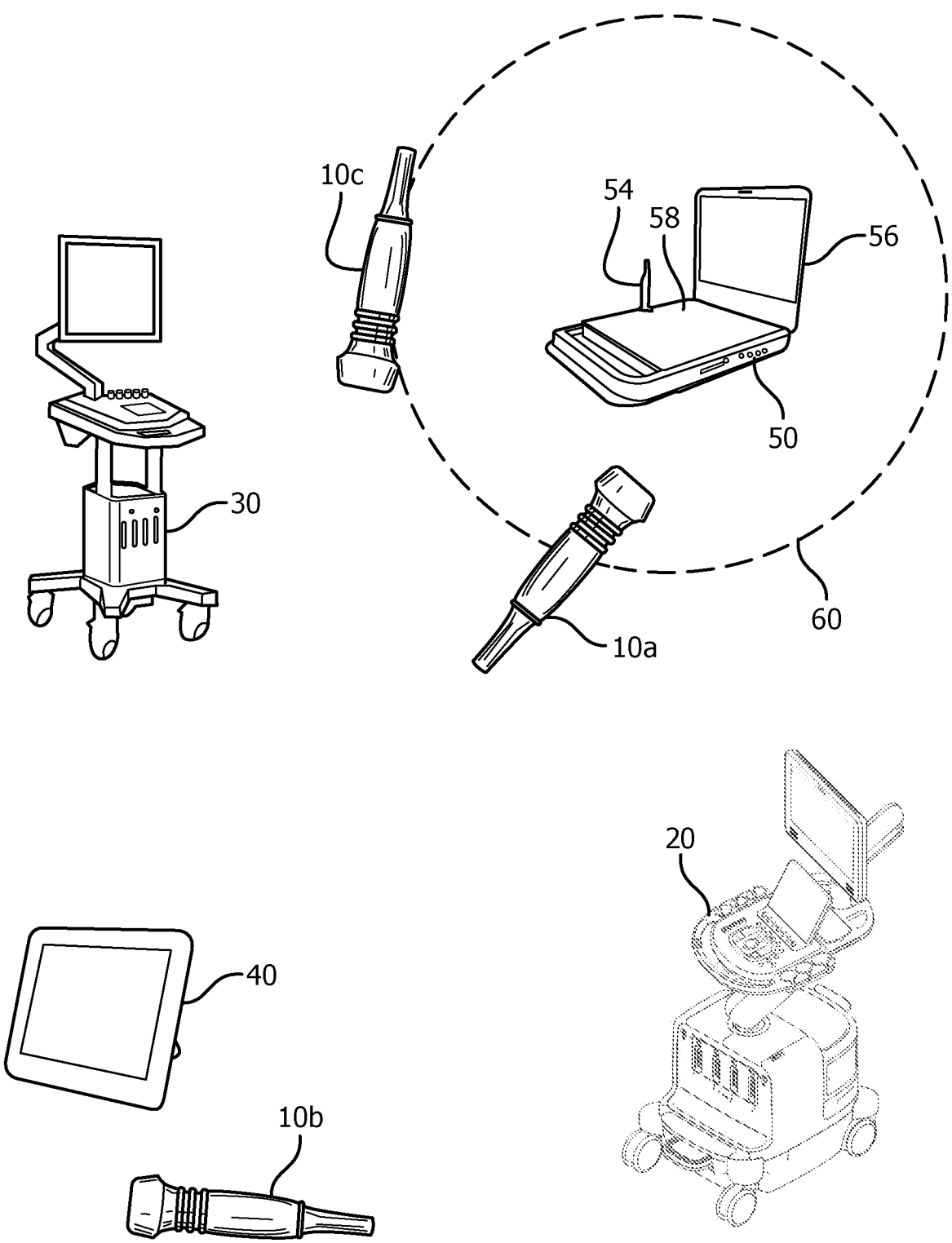
FIG. 1 illustrates an ultrasound lab with several wireless probes and four mobile ultrasound systems capable of communicating with the wireless probes.

FIG. 1 depicts an ultrasound lab with four mobile ultrasound systems in it, a premium Epiq system 20, a midrange ClearVue system 30, a tablet style Visiq system 40, and a laptop style CX50 system 50, all made by Philips Healthcare of Andover, Mass., USA. In this example, all of the ultrasound systems have wireless capability and so are able to work with wireless ultrasound probes. Also in the lab are three wireless probes, including probe 10a which is being used with the laptop system 50 and probe 10b which is being used with the tablet system 40. The third probe 10c is in the process of being carried through the lab to be used with the premium system 20. As it does so in this example, it passes into close proximity with the laptop system 50. If the pairing protocol used by these systems and probes would pair a probe and system which are in closest proximity, the in-transit probe 10c could pair with the laptop system 50 as it passes close to the antenna 54 of the laptop system's radio. This undesired pairing would disrupt the intended use of probe 10a with the laptop system 50, and illustrates a problem with proximity pairing which must be addressed.

FIG. 1 also illustrates a dashed circle 60 which in this example is marking the outer boundary of a spherical one meter distance from the radio antenna 54 of the laptop system 50. The problem just described is prevented in accordance with the present invention by bringing a probe 10a within one meter or less of the antenna 54 in order to pair the probe 10a with ultrasound system 50. Once the probe 10a is within this distance from the antenna, pairing can proceed either automatically or with user assistance such as by touching or clicking a "Pair" button on the display screen 56 or control panel 58 of the ultrasound system 50. The probe 10c remains paired with the ultrasound system 50 until the user affirmatively de-associates the probe from the system as by touching or clicking an "End Exam" button on the system; or turns off the probe; or the probe goes out of range of the radio of system 50 for an extended period of time, a length of time which can be determined by the user during system setup. A pairing and de-association procedure such as this will prevent the foregoing problem from happening. If someone passes by carrying a powered-on wireless probe 10c that is within radio range of system 50, pairing will not occur because the transported probe is not within the one meter distance required for pairing. And even if the transported probe passes within the one meter distance and even is in closer proximity to antenna 54 than is probe 10a, no pairing will occur because probe 10a has been previously paired with the system and is in use with (within radio range of) the system.

Figure 2:
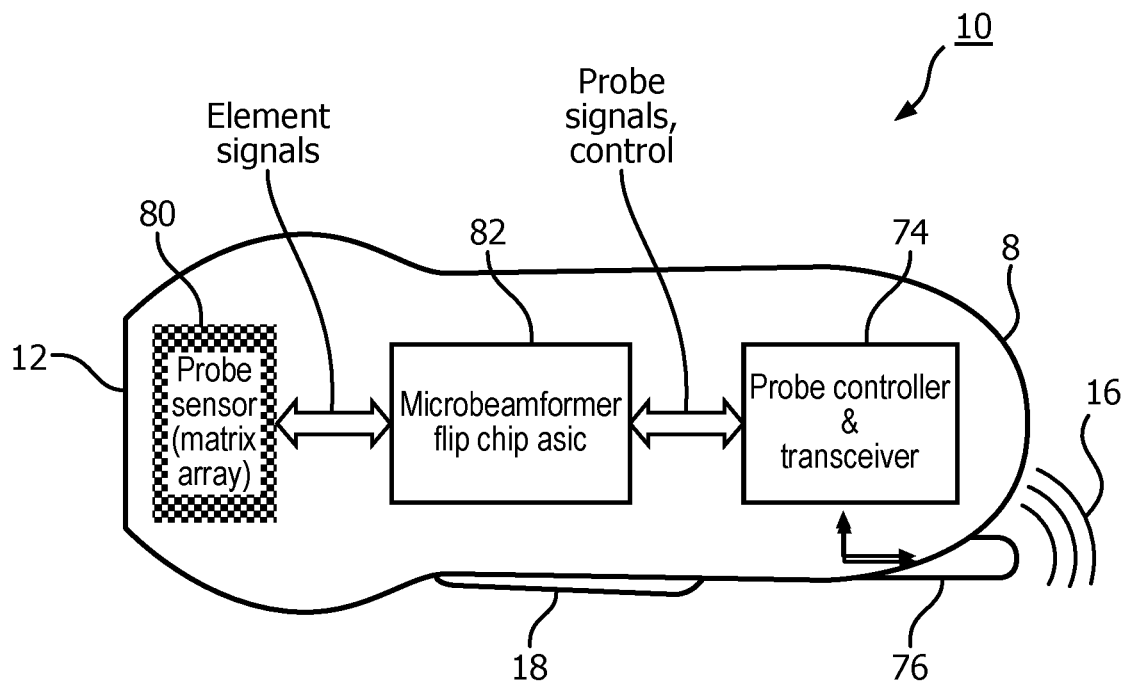
FIG. 2 illustrates the functional components of a wireless 2D array probe.

The pairing procedure of the present invention may be implemented with a wireless ultrasound probe such as that shown in FIG. 2. In order to scan a two dimensional image plane the probe 10 uses a one-dimensional (1D) transducer array located at the distal end 12 of the probe at the acoustic window of the probe. For both two dimensional and three dimensional electronic scan imaging, the probe uses a 2D matrix array transducer 80 as shown in this example. The transducer array is formed of ceramic piezoelectric transducer elements, a piezoelectric polymer (PVDF), or may be a semiconductor-based micromachined ultrasound transducer (MUT) such as a PMUT (piezoelectric MUT) or a CMUT (capacitive MUT) array of elements. The array transducer 80 is driven by, and echoes are processed by, one or more microbeamformer ASICs 82. The microbeamformer 82 receives echo signals from the elements of the transducer array 80 and delays and combines the per-element echo signals into a small number of partially beamformed signals. For instance the microbeamformer 82 can receive echo signals from a row of 128 transducer elements of the array and combine these signals to form eight partially beamformed signals, thereby reducing the number of signal paths from 128 to eight. The microbeamformer 82 can also be implemented to produce fully beamformed signals from all of the elements of the active aperture as described in U.S. Pat. No. 6,142,946 (Hwang et al.) In a preferred embodiment fully beamformed and detected signals are produced by the probe for wireless transmission to the host ultrasound system so as to reduce the data rate to one which accommodates acceptable real time imaging frame rates. Microbeamformer technology suitable for use in beamformer 82 is described in U.S. Pat. No. 5,229,933 (Larson III); U.S. Pat. No. 6,375,617 (Fraser); and U.S. Pat. No. 5,997,479 (Savord et al.) The beamformed echo signals are coupled to a probe controller and transceiver subsystem 74 which transmits the beamformed signals to a host system, the mainframe ultrasound system such as ultrasound system 20, 30, 40 or 50, where the partially beamformed signals undergo further beamforming and then image processing and display. The probe controller and transceiver subsystem 74 also receives control signals from the host system when the probe is controlled from the host, and couples corresponding control signals to the microbeamformer 82 to, for example, steer and focus beams at a desired depth or transmit and receive signals of a desired mode (Doppler, B mode) to and from a desired location of an image region. Not shown in this illustration are the power subsystem and battery to power the probe, which are described below.

The transceiver of the probe controller and transceiver subsystem 74 transmits and receives r.f. signals 16 by means of an internal or stub antenna 76, similar to that of a cellphone. The stub antenna provides one of the same benefits as it does on a cellphone, which is that its small profile makes it convenient to hold and carry and reduces the possibility of damage. However in this embodiment of a wireless probe, the stub antenna 76 serves an additional purpose. When a sonographer holds a conventional cabled probe, the probe is grasped from the side as if holding a thick pencil. A wireless probe such as that of FIG. 2 can be held in the same manner, however, since the probe has no cable, it can also be held by grasping the proximal end of the probe. This cannot be done with a conventional cabled probe due to the presence of the cable. A wireless probe user may want to hold the wireless probe by the proximal end in order to exert a large amount of force against the body for good acoustic contact. However, wrapping the hand around the proximal end of the probe, when the antenna is inside the proximal end of the probe, will at least partially shield the antenna from signal transmission and reception and may cause unreliable communication. It has been found that using an antenna which projects from the proximal end of the probe not only extends the antenna field well outside the probe case 8, but also discourages the user from holding the probe by the proximal end due to the discomfort of pressing against the stub antenna. Instead, the user is more likely to grasp the probe from the side in the conventional manner, leaving the antenna field exposed for good signal transmission and reception. For good reception the antenna configuration of the base station host can introduce some diversity against polarization and orientation effects by producing two complementary beam patterns with different polarizations. Alternatively, the antenna can be a single high performance dipole antenna with a good single polarization beam pattern. With the antenna at the proximal end of the probe, the probe beam pattern can extend radially with respect to the longitudinal axis of the probe, and readily intersect the beam pattern of the base station host. Such a probe beam pattern can be effective with antennas of the base station host located at the ceiling, as may be done in a surgical suite. Reception has also been found to be effective with this probe beam pattern from reflections by room walls and other surfaces, which are often close to the site of the ultrasound procedure, such as a diagnostic imaging exam. Typically a ten meter range is sufficient for most exams, as the probe and base station host are in close proximity to each other. Communication frequencies employed can be in the 4 GHz range, and suitable polymers for the probe case 8 such as ABS are relatively transparent to r.f. signals at these frequencies. R.f. communication can be improved at the base station host, where multiple antennae can be employed for improved diversity in embodiments where multiple antennae are not cumbersome as they would be for the wireless probe. See, for example, International Patent Publication WO 2004/051882, entitled "Delay Diversity In A Wireless Communications System." The multiple antennae can utilize different polarizations and locations to provide reliable communications even with the varying linear and angular orientations assumed by the probe during the typical ultrasound exam. The typical probe manipulation can roll the probe throughout a 360° range of rotation and tilt angles through approximately a hemispherical range of angles centered on vertical. Hence, a dipole radiation pattern centered on the center longitudinal axis of the probe will be optimal for a single antenna and a location at the proximal end has been found to be most desirable. The antenna pattern can be aligned exactly with this center axis, or offset but still in approximate parallel alignment with this center axis.

Figure 3:
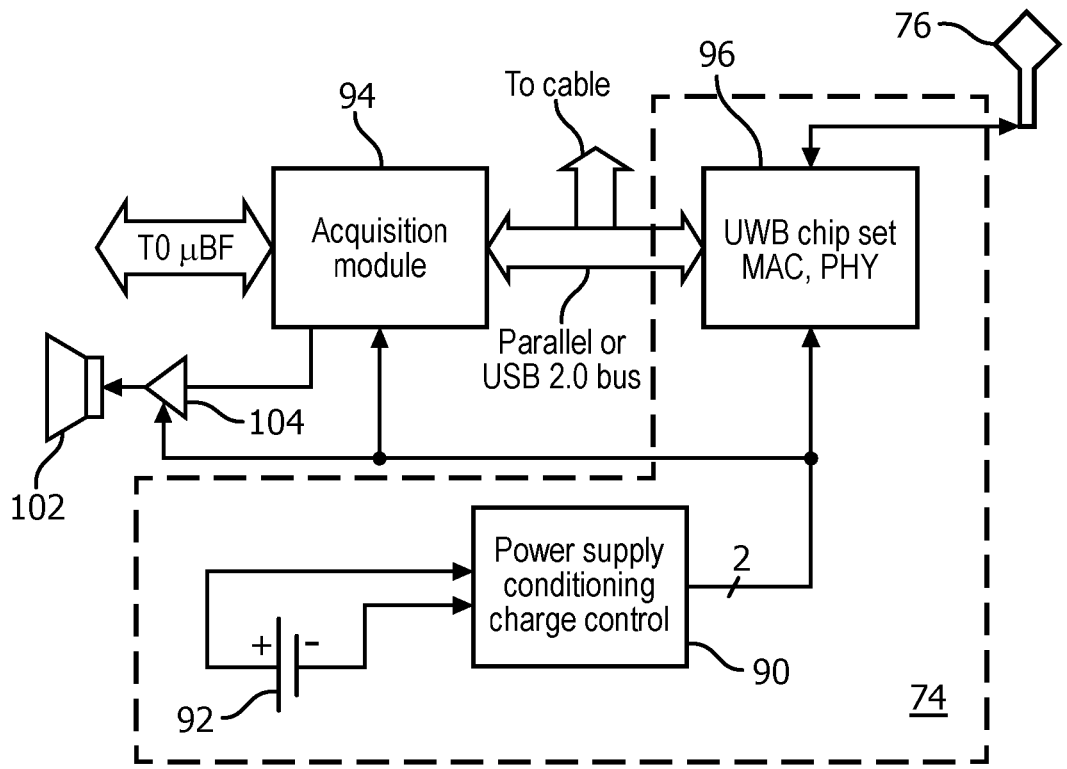
FIG. 3 illustrates in block diagram form the major electronic subsystems between the microbeamformer and antenna of the wireless probe of FIG. 2.

A typical probe controller and transceiver subsystem for a wireless probe is shown in FIG. 3. A battery 92 powers the wireless probe and is coupled to a power supply and conditioning circuit 90. The power supply and conditioning circuit translates the battery voltage into a number of voltages required by the components of the wireless probe including the transducer array. A typical constructed probe may require nine different voltages, for example. The power supply and conditioning circuit also provides charge control during the recharging of the battery 92. In a constructed embodiment the battery is a lithium polymer battery which is prismatic and can be formed in a suitable shape for the available battery space inside the probe case.

An acquisition module 94 provides communication between the microbeamformer and the transceiver. The acquisition module provides timing and control signals to the microbeamformer, directing the transmission of ultrasound waves and receiving at least partially beamformed echo signals from the microbeamformer, which are demodulated and detected (and optionally scan converted) and communicated to the transceiver 96 for transmission to the base station host. In this example the acquisition module communicates with the transceiver over a parallel or a USB bus so that the probe can be used with a USB cable when desired. If a USB or other bus is employed, it can provide an alternative wired connection to the base station host over a cable, thus bypassing the transceiver portion 96 and becoming a wired probe.

Also coupled to the acquisition module 94 and powered by the power supply and conditioning circuit 90 is a loudspeaker 102, driven by an amplifier 104, which produces audible tones or sounds. In a preferred embodiment the loudspeaker 102 is a piezoelectric loudspeaker located inside the case 8 and which may be behind a membrane or the wall of the case for good acoustics and sealing. The loudspeaker can be used to produce a variety of sounds or tones or even voice messages. The loudspeaker has a variety of uses. If the wireless probe is moved too far away from the host so that there is unreliable reception or even a complete loss of signal by the host or the probe, the loudspeaker can beep to alert the user. The loudspeaker can also emit a unique tone when the probe is within the one meter pairing distance. The loudspeaker can beep when the battery charge is low. The loudspeaker can emit a tone when the user presses a button or control on the probe, providing audible feedback of control activation. The loudspeaker can provide haptic feedback based upon the ultrasound examination. The loudspeaker can emit a sound when a paging control is activated to locate the probe. The loudspeaker can produce audio Doppler sounds during a Doppler exam, or heart sounds when the probe is used as an audio stethoscope.

The transceiver in this example is an ultra wideband chip set 96, although it can also be a WiFi (802.11 standard) radio or other standard radio. An ultra wideband transceiver was found to have a data communication rate which provides acceptable real time imaging frame rates as well as acceptable range for an acceptable level of battery power consumption. Ultra wideband chip sets are available from a variety of sources such as Starix of Irvine, Calif. and Alereon of Austin, Tex. WiFi radio adapters such as the Netgear N300 wireless-N USB adapter are also suitable for wireless WiFi communication.

Figure 4A:
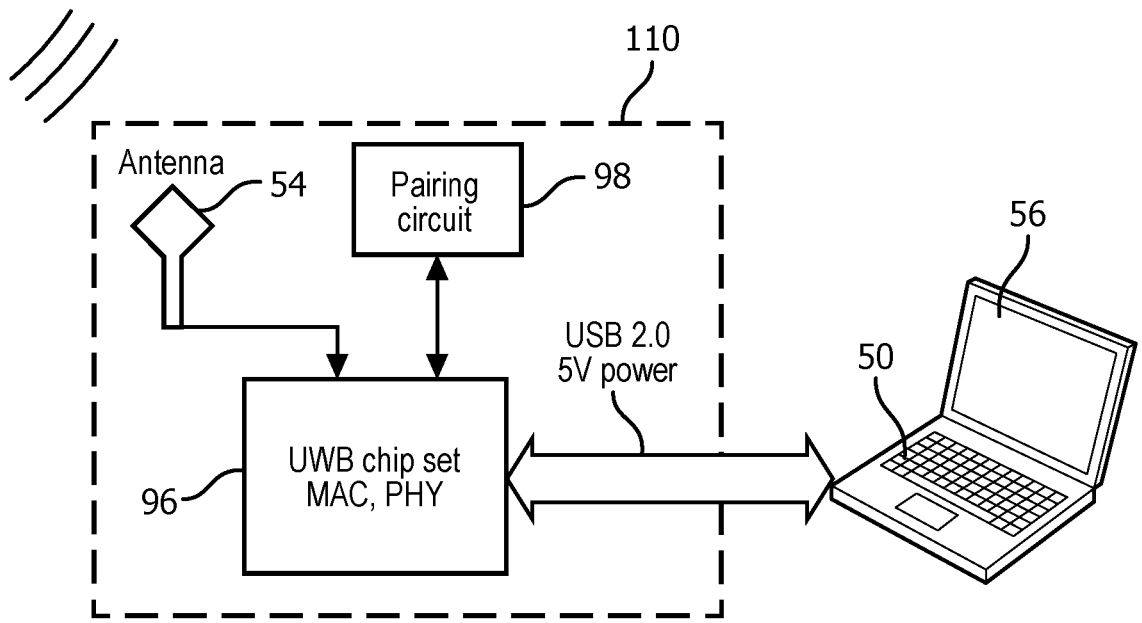
FIG. 4a illustrates in block diagram form the major components of a radio module for a mobile ultrasound system constructed in accordance with the principles of the present invention which is capable of communicating with the probe of FIG. 2.
Figure 4B:
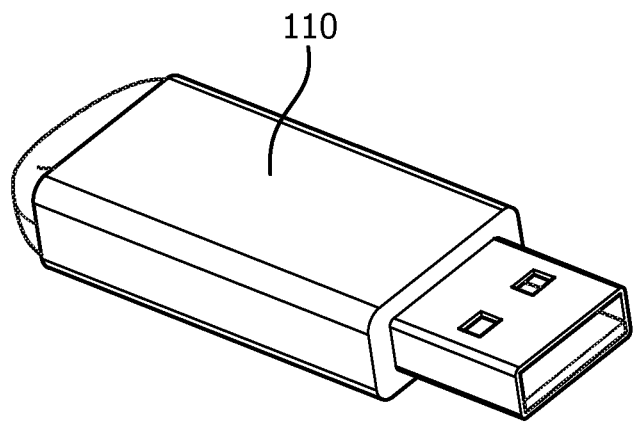
FIG. 4b illustrates the packaging of the radio module of FIG. 4a, which is configured as a USB stick.

FIG. 4a illustrates the wireless probe signal path at the base station host, here shown in the laptop system configuration 50. The antenna 54 is coupled to an identical or compatible ultra wideband chip set 96 which performs transception at the host. In a preferred embodiment for the laptop configuration, the antenna 54 and ultra wideband chip set are configured as a USB-connectible "dongle" 110 as shown in FIG. 4b, which plugs into and is powered by a USB port of the host system 50. The optional USB link between probe and the host laptop allows charging of the battery in the probe, via the power connection, or wired data transfer when preferred over wireless operation. Further details of the wireless probe and mobile ultrasound system shown in FIGS. 2-4b may be found in US pat. pub. no. 2010/0168576 (Poland et al.)

In accordance with the principles of the present invention, the USB radio module 110 also includes a pairing circuit 98. While the pairing circuit 98 in this example is shown located in the radio module 110, it could also be implemented in the ultrasound system. The pairing circuit responds to a pairing request from a wireless probe, such as the presence of a wireless probe within the one meter pairing distance, verifies that the probe is within the pairing distance and, if so, commands the ultrasound system 50 to proceed with the pairing protocol.

Figure 5:
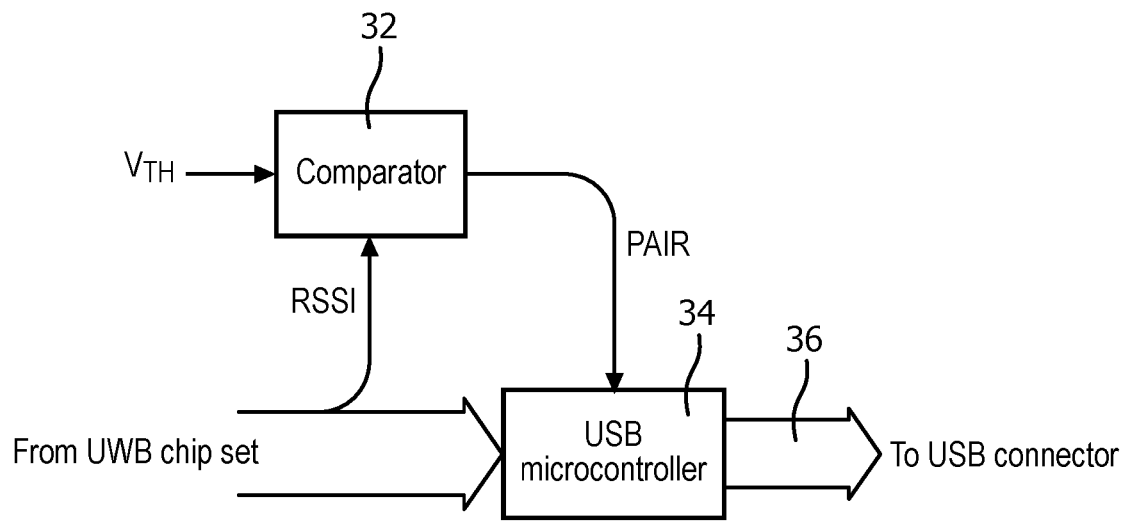
FIG. 5 illustrates in block diagram form the components of the pairing circuit of FIG. 4a and their interface with other components of the USB stick.

One implementation of a pairing circuit 98 is shown in FIG. 5. Radios such as the UWB chip set commonly produce a signal indicating the strength of received signals known as the received signal strength indicator (RSSI). An equivalent signal can be produced by envelope-detecting a received probe radio signal, which also indicates the strength (amplitude) of the received signal. The RSSI signal from the UWB chip set is coupled to one input of a comparator 32, which compares the RSSI with a threshold voltage $V_{TH}$. This threshold voltage is preset and is approximately equal to the RSSI produced in response to signals from a wireless probe when the probe is one meter from the radio antenna. Thus, a wireless probe which is one meter from the mobile system 50 or closer will transmit signals to the system radio which produce an RSSI which equals or exceeds $V_{TH}$. When that happens, the comparator 32 produces a PAIR signal which is coupled to a low power USB microcontroller 34 along with the data received from the wireless probe by the UWB chip set. The received data includes the unique identifier of the wireless probe. The USB microcontroller couples the PAIR signal to the USB connector of the radio module 110 so that the mobile ultrasound system 50 receives the PAIR signal in USB format. The ultrasound system is thereby notified that a wireless probe has been identified in pairing range and the system responds by reading the probe's unique identifier on the USB data bus 36 and selecting this identifier as the one with which to pair. The ultrasound system and probe then exchange pairing protocol data as is known in the art and the communication between the wireless probe and ultrasound system is established. This exclusive communication connection remains in place unless the user affirmatively ends it as by pressing a control button; or turns off the wireless probe; or does not use the communication link or is out of radio range for a predetermined extended period of time, whereupon the connection times out and is ended by the system or probe.

Figure 6:
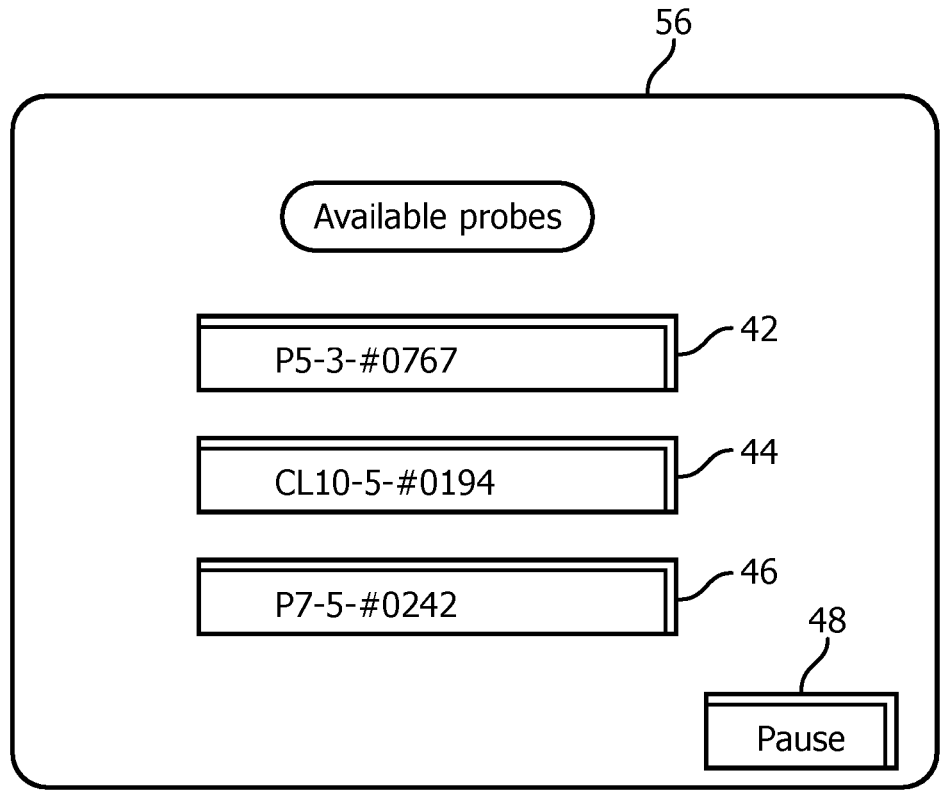
FIG. 6 illustrates a display screen of a mobile ultrasound system showing a variety of wireless probes which can be paired with the ultrasound system.

To aid the user in reliably pairing with a specific wireless probe, the mobile ultrasound system can produce a display of the wireless probes within radio range as shown in FIG. 6. In this example the display screen 56 is showing a list of wireless probes identified to be within radio range, as indicated by their transmitted unique identifier signals. The identified probes are preferably listed on the screen in received signal strength order so that the probe nearest to the ultrasound system will be at the top of the list. The ultrasound system uses the RSSI to order the list of probes, each of which is displayed on a screen button 42, 44, or 46. In this example each probe also has a unique number, which is printed on a label on each probe. In this example the user at the ultrasound system is holding a P5-3 wireless probe with the number "#0767" on it. The user can thus look at the number on the physical probe and the number of the identified wireless probe at the top of the list and know that a selection of the top probe on the screen list will pair the probe she is holding. The user clicks on button 42 on the screen and the ultrasound system proceeds to execute the protocol necessary to pair with the correct probe.

In this example the mobile ultrasound system also displays a "Pause" user control button 48 in the lower right corner of the screen, which is available while a wireless probe is paired with the system. When the user wants to temporarily suspend an exam for another activity, such as taking a phone call or having a discussion with a colleague, the user clicks on the Pause button 48. This action informs the ultrasound system that, even though the wireless probe is currently not being used to scan a patient, the system is to remain paired with the wireless probe and not break the communication. The system and probe will thus remain in communication, awaiting continuance of the exam until overridden by another action such as the communication link being affirmatively ended by the user, the probe or system being turned off, the two being out of radio range for an extended time, or depletion of the battery charge of the wireless probe.

What is claimed is:

1. A method for pairing a wireless ultrasound probe with a mobile ultrasound system having a radio comprising:
    locating a wireless ultrasound probe with a radio within a predetermined range of a mobile ultrasound system with a radio;
    determining, at the mobile ultrasound system, that the wireless ultrasound probe present is within the predetermined range;
    determining, at the mobile ultrasound system, whether the mobile ultrasound system is in communication with another wireless ultrasound probe; and
    pairing the wireless ultrasound probe and mobile ultrasound system to be in communication with each other when the mobile ultrasound system is determined not to be in communication with another wireless ultrasound probe.

2. The method of claim 1, wherein the predetermined range comprises one meter.

3. The method of claim 2, wherein the predetermined range is a distance of one meter from an antenna of the mobile ultrasound system radio.

4. The method of claim 1, wherein the ultrasound system radio and the wireless probe radio are both ultra wideband transceivers.

5. The method of claim 1, wherein the ultrasound system radio and the wireless probe radio are both WiFi (802.11) standard transceivers.

6. The method of claim 1, wherein determining further comprises receiving with the ultrasound system radio a radio signal from the wireless probe and producing a signal indicating a strength of the received signal.

7. The method of claim 6, wherein producing further comprises producing a received signal strength indicator (RSSI) signal by the ultrasound system radio.

8. The method of claim 6, wherein determining further comprising comparing the signal indicating the strength of the received signal to a threshold voltage.

9. The method of claim 8, wherein the threshold voltage is equal to the signal indicating the strength of the received signal when the wireless probe is at the predetermined range from the ultrasound system.

10. The method of claim 1, further comprising maintaining a communication link established by the pairing until:
    receiving a de-association to end the pairing; or
    detecting that the wireless ultrasound probe is turned off; or
    detecting that the wireless ultrasound probe has been out of range of the mobile ultrasound system for a long period of time; or
    detecting that communication of new data over the link has been idle for a preset period of time.

11. The method of claim 1, further comprising:
    conducting an ultrasound exam with the paired wireless ultrasound probe and mobile ultrasound system;
    suspending the ultrasound exam; and
    actuating a user control of the mobile ultrasound system to maintain the paired communication during suspension of the ultrasound exam.

12. A method for pairing one of a plurality of wireless ultrasound probes that are within radio range of a mobile ultrasound system with the mobile ultrasound system comprising:
    locating a plurality of wireless ultrasound probes, each having a radio, within radio range of a mobile ultrasound system having a radio;
    receiving, with the radio of the mobile ultrasound system, a unique identifier signal from each of the wireless ultrasound probes;
    displaying on a display of the mobile ultrasound system the identities of the wireless ultrasound probes in correspondence with the unique identifier signals;
    determining, at the mobile ultrasound system, whether the mobile ultrasound system is in communication with another wireless ultrasound probe; and
    pairing a particular wireless ultrasound probe and the mobile ultrasound system by selecting the displayed identity of the particular wireless ultrasound probe when the mobile ultrasound system is determined not to be in communication with another wireless ultrasound probe.

13. The method of claim 12, wherein displaying further comprises displaying the identities of the wireless ultrasound probes in order of strengths of signals received from the probes.

14. The method of claim 12, wherein displaying further comprises displaying the identity of a wireless ultrasound probe only if it is within a predetermined distance of the mobile ultrasound system; and
    wherein pairing further comprises selecting the displayed wireless ultrasound probe for pairing.

15. The method of claim 12, further comprising maintaining a communication link established by the pairing until:
    receiving a de-association to end the pairing; or
    detecting that the particular wireless ultrasound probe is turned off; or
    detecting that the particular wireless ultrasound probe has been out of range of the mobile ultrasound system for a long period of time; or
    detecting that communication of new data over the link has been idle for a preset period of time.

* * * * *